(12) United States Patent
Mujwid et al.

(10) Patent No.: US 9,060,837 B2
(45) Date of Patent: Jun. 23, 2015

(54) PATTERNED SLING IMPLANT AND METHOD

(75) Inventors: James R. Mujwid, Crystal, MN (US); Jessica L. Roll, Maple Grove, MN (US); Karl A. Jagger, Deephaven, MN (US); Robert C. Grant, Minneapolis, MN (US)

(73) Assignee: AMS Research Corporation, Minnetonka, MN (US)

( * ) Notice: Subject to any disclaimer, the term of this patent is extended or adjusted under 35 U.S.C. 154(b) by 392 days.

(21) Appl. No.: 12/964,502

(22) Filed: Dec. 9, 2010

(65) Prior Publication Data

US 2011/0124956 A1 May 26, 2011

Related U.S. Application Data

(63) Continuation-in-part of application No. 12/953,268, filed on Nov. 23, 2010.

(60) Provisional application No. 61/263,557, filed on Nov. 23, 2009, provisional application No. 61/267,888, filed on Dec. 9, 2009, provisional application No. 61/291,385, filed on Dec. 31, 2009.

(51) Int. Cl.
*A61F 2/02* (2006.01)
*A61F 13/00* (2006.01)
*A61F 5/00* (2006.01)
*A61F 2/00* (2006.01)
(Continued)

(52) U.S. Cl.
CPC ......... *A61F 2/0045* (2013.01); *A61B 17/06109* (2013.01); *A61B 2017/00805* (2013.01); *A61F 2002/0081* (2013.01); *A61F 2220/0016* (2013.01)

(58) Field of Classification Search
CPC ................... A61B 2017/00805; A61F 2/0004; A61F 2/0031; A61F 2/0036; A61F 2/0045; A61F 2/0063; A61F 2002/0068
USPC ....................................................... 600/30, 37
See application file for complete search history.

(56) References Cited

U.S. PATENT DOCUMENTS

| 3,054,406 A | 9/1962 | Usher |
| 3,124,136 A | 3/1964 | Usher |

(Continued)

FOREIGN PATENT DOCUMENTS

| EP | 1060714 A3 | 9/2002 |
| IT | 1299162 | 4/1998 |

(Continued)

OTHER PUBLICATIONS

Advantage A/T™, Surgical Mesh Sling Kit, Boston Scientific, 6 pages (2002).

(Continued)

*Primary Examiner* — Jacqueline Cheng
*Assistant Examiner* — Kaylee Wilson
(74) *Attorney, Agent, or Firm* — Gregory L. Koeller (57) ABSTRACT

Embodiments of elongate pelvic implants and methods for treating pelvic conditions, such as incontinence, are provided. The implants can include a tissue support portion, one or more extension portions and one or more anchors. The implant is constructed as a unitary sling implant. The implant can be constructed or formed in a generally elongate shape to provide a lattice support structure of repeated cells.

18 Claims, 12 Drawing Sheets

(51) Int. Cl.
*A61B 17/06* (2006.01)
*A61B 17/00* (2006.01)

(56) References Cited

U.S. PATENT DOCUMENTS

| | | | |
|---|---|---|---|
| 3,384,073 | A | 5/1968 | Van Winkle, Jr. |
| 3,789,828 | A | 2/1974 | Schulte |
| 4,548,202 | A | 10/1985 | Duncan |
| 4,775,380 | A | 10/1988 | Seedhom et al. |
| 4,865,031 | A | 9/1989 | O'Keeffe |
| 5,032,508 | A | 7/1991 | Naughton et al. |
| 5,919,232 | A | 7/1999 | Chaffringeon et al. |
| 6,010,447 | A | 1/2000 | Kardjian |
| 6,031,148 | A | 2/2000 | Hayes et al. |
| 6,482,214 | B1 | 11/2002 | Sidor, Jr. et al. |
| 6,599,323 | B2 | 7/2003 | Melican et al. |
| 6,638,284 | B1 | 10/2003 | Rousseau et al. |
| 6,691,711 | B2 | 2/2004 | Raz |
| 6,884,212 | B2 | 4/2005 | Thierfelder et al. |
| 6,953,428 | B2 | 10/2005 | Gellman et al. |
| 7,025,063 | B2 | 4/2006 | Snitkin |
| 7,087,065 | B2 | 8/2006 | Ulmsten et al. |
| 7,131,943 | B2 | 11/2006 | Kammerer |
| 7,131,944 | B2 | 11/2006 | Jacquetin |
| 7,175,591 | B2 | 2/2007 | Kaladelfos |
| 7,303,525 | B2 | 12/2007 | Watschke et al. |
| 7,347,812 | B2 | 3/2008 | Mellier |
| 7,351,197 | B2 | 4/2008 | Montpetit et al. |
| 7,393,320 | B2 | 7/2008 | Montpetit et al. |
| 7,407,480 | B2 | 8/2008 | Staskin |
| 7,422,557 | B2 | 9/2008 | Arnal |
| 7,500,945 | B2 | 3/2009 | Cox |
| 7,513,865 | B2 | 4/2009 | Bourne et al. |
| 7,601,118 | B2 | 10/2009 | Smith et al. |
| 7,722,527 | B2 | 5/2010 | Bouchier et al. |
| 7,722,528 | B2 | 5/2010 | Arnal et al. |
| 7,762,969 | B2 | 7/2010 | Gellman et al. |
| 2002/0028980 | A1 | 3/2002 | Thierfelder et al. |
| 2002/0099258 | A1* | 7/2002 | Staskin et al. ............ 600/29 |
| 2002/0103542 | A1 | 8/2002 | Bilbo |
| 2002/0138025 | A1 | 9/2002 | Gellman et al. |
| 2002/0147382 | A1 | 10/2002 | Neisz et al. |
| 2002/0151762 | A1 | 10/2002 | Rocheleau |
| 2003/0004581 | A1 | 1/2003 | Rousseau |
| 2004/0122474 | A1* | 6/2004 | Gellman et al. ............ 606/232 |
| 2005/0004427 | A1 | 1/2005 | Cervigni |
| 2005/0234291 | A1* | 10/2005 | Gingras ............ 600/30 |
| 2005/0256530 | A1* | 11/2005 | Petros ............ 606/151 |
| 2005/0277806 | A1 | 12/2005 | Cristalli |
| 2006/0229493 | A1 | 10/2006 | Weiser et al. |
| 2006/0229596 | A1 | 10/2006 | Weiser et al. |
| 2007/0299300 | A1* | 12/2007 | Smith et al. ............ 600/30 |
| 2008/0132754 | A1 | 6/2008 | Thierfelder et al. |
| 2009/0149700 | A1* | 6/2009 | Garcia et al. ............ 600/37 |
| 2010/0261955 | A1 | 10/2010 | O'Hern et al. |

FOREIGN PATENT DOCUMENTS

| | | | |
|---|---|---|---|
| WO | WO9317635 A1 | 9/1993 | |
| WO | WO0057812 A1 | 10/2000 | |
| WO | WO0106951 A1 | 2/2001 | |
| WO | WO0156499 A1 | 8/2001 | |
| WO | WO0222184 A2 | 3/2002 | |
| WO | WO02091950 A1 | 11/2002 | |
| WO | WO03028585 A2 | 4/2003 | |
| WO | WO03037215 A2 | 5/2003 | |
| WO | WO03041613 A1 | 5/2003 | |
| WO | WO03096929 A1 | 11/2003 | |
| WO | WO2004045457 A1 | 6/2004 | |
| WO | WO2005094741 A1 | 10/2005 | |
| WO | WO2007097994 | 8/2007 | |
| WO | WO2008057261 A2 | 5/2008 | |
| WO | WO 2008152435 A1 * | 12/2008 | ............ A61F 2/00 |

OTHER PUBLICATIONS

Cervigni, Mauro et al., The Use of Synthetics in the Treatment of Pelvic Organ Prolapse, Voiding Dysfunction and Female Urology, vol. 11, pp. 429-435 (2001).

Debodinance, Philipp et al., "Tolerance of Synthetic Tissues in Touch With Vaginal Scars: Review to the Point of 287 Cases", Europeon Journal of Obstetrics & Gynecology and Reproductive Biology 87 (1999) pp. 23-30.

Diana, et al., Treatment of Vaginal Vault Prolapse With Abdominal Sacral Colpopexy Using Prolene Mesh, American Journal of Surgery, vol. 179, pp. 126-128, (Feb. 2000).

Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).

Flood, C.G. et al., Anterior Colporrhaphy Reinforce With Marlex Mesh for the Treatment of Cystoceles, International Urogynecology Journal, vol. 9, pp. 200-204 (1998).

Gynecare TVT Tension-Free Support for Incontinence. The tension-free solution to female Incontinence, Gynecare Worldwide, 6 pages, (2002).

IVS Tunneller—A Universal instrument for anterior and posterior intra-vaginal tape placement, Tyco Healthcare, 4 pages (Aug. 2002).

Julian, Thomas, The Efficacy of Marlex Mesh in the Repair of Sever, Recurrent Vaginal Prolapse of the Anterior Midvaginal Wall, Am J Obstet Gynecol, vol. 175, n. 6, pp. 1472-1475 (Dec. 1996).

Lichtenstein, Irving L. et al, The Tension Free Hernioplasty, The American Journal of Surgery, vol. 157 pp. 188-193 (Feb. 1989).

Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).

Migliari, Roberto et al., Tension-Free Vaginal Mesh Repair for Anterior Vaginal Wall Prolapse, Eur Urol, vol. 38, pp. 151-155 (Oct. 1999).

Migliari, Roberto et al., Treatment Results Using a Mixed Fiber Mesh in Patients With Grade IV Cystocele, Journal of Urology, vol. 161, pp. 1255-1258 (Apr. 1999).

Moir, J. Chassar et.al., The Gauze-Hammock Operation, The Journal of Obstetrics and Gynaecology of British Commonwealth, vol. 75 No. 1, pp. 1-9 (Jan. 1968).

Nichols, David H., The Mersilene Mesh Gauze-Hammock for Severe Urinary Stress Incontinence, Obstetrics and Gynecology. vol. 41, pp. 88-93 (Jan. 1973).

Nicita, Giulio, A New Operation for Genitourinary Prolapse, Journal of Urology, vol. 160, pp. 741-745 (Sep. 1998).

Niknejad, Kathleen et al., Autologous and Synthetic Urethral Slings for Female Incontinence, Urol Clin N Am, vol. 29, pp. 597-611 (2002).

Richardson, David A. et al., Delayed Reaction to the Dacron Buttress Used in Urethropexy, The Journal of Reproductive Medicine, pp. 689-692, vol. 29, No. 9 (Sep. 1984).

Sanz, Luis E. et al., Modification of Abdominal Sacrocolpopexy Using a Suture Anchor System, The Journal of Reproductive Medicine, vol. 48, n. 7, pp. 496-500 (Jul. 2003).

Sergent, F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-126 (Apr. 2003).

Sullivan, Eugene S. et al., Total Pelvic Mesh Repair a Ten-Year Experience, Dis. Colon Rectum, vol. 44, No. 6, pp. 857-863 (Jun. 2001).

Pourdeyhimi, B. Porosity of Surgical Mesh Fabrics: New Technology, J. Biomed. Mater. Res.: Applied Biomaterials, vol. 23, No. A1, pp. 145-152 (1989).

Brochure, "GPS for Pelvic Floor Repair," Gynecare Prolift, 6 pages, 2005.

* cited by examiner

PATTERNED SLING IMPLANT AND METHOD

PRIORITY

This application is a Continuation-in-Part Application of U.S. application Ser. No. 12/953,268, filed Nov. 23, 2010, which claims priority to and the benefit of U.S. Provisional Application No. 61/263,557, filed Nov. 23, 2009, and this Application also claims priority to and the benefit of U.S. Provisional Application No. 61/267,888, filed Dec. 9, 2009, and U.S. Provisional Application No. 61/291,385, filed Dec. 31, 2009, with each application incorporated herein by reference in its entirety.

FIELD OF THE INVENTION

The present invention relates generally to surgical methods and apparatus and, more specifically, to surgically implantable sling devices and methods for forming and using the same.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Urinary incontinence can be characterized by the loss or diminution in the ability to maintain the urethral sphincter closed as the bladder fills with urine. Male or female SUI generally occurs when the patient is physically stressed.

Many strategies have been implemented over the years to provide mesh implants adapted to enhance therapeutic support of the respective pelvic tissues. For instance, sling and other implant devices are known to provide support of the urethra or bladder neck in treating urinary incontinence in patients.

Many of the implants promoted for treating incontinence and other pelvic disorders were born from and inherited the material and geometric restraints of existing stent and hernia implants. While objectively effective in their respective applications, such stent and hernia implants are naturally constructed to address very different issues. Namely, the requisite barrier, rigidity and tissue integration and compatibility needs of a hernia mesh or vascular stent implant can be very disparate from the implant characteristics required in treating pelvic incontinence.

Although these traditional mesh implants have had a tremendous benefit for those suffering from incontinence, there is still room for improvement. As a result, there is a desire to obtain a uniquely applicable, minimally invasive and highly effective implantable sling support that can be used to treat incontinence or other pelvic disorders and conditions.

SUMMARY OF THE INVENTION

The present invention describes sling implants and methods for treating pelvic conditions such as incontinence (various forms such as fecal incontinence, stress urinary incontinence, urge incontinence, mixed incontinence, etc.) and other conditions caused by muscle and ligament weakness. Other uses include providing a support or platform for plastic surgery, hernia repair, and ortho repairs and support, to name a few. Embodiments of the implants can include a tissue support portion, one or more extension portions and one or more anchors. Certain embodiments can be constructed as a unitary sling implant. The implant can be constructed or formed in a generally elongate or rectangular shape, or take on a myriad of other compatible configurations or shapes. The support portion is adapted for positioning and support under tissue or organs, such as the urethra or bladder. The extension portions extend out from the support portion such that the anchors or anchoring features can be deployed for tissue fixation.

In various embodiments, the implants can be formed of patterned cells by way of a molding, die casting, laser etching, laser cutting, extruding, punching, 3-D printing and the like. Such a pattern cut or formed implant can be constructed of a polymer material to provide a lattice support structure of repeated cells. Unlike woven or knitted conventional implants, embodiments of the present invention are a homogeneous unitary construct.

Portions of the implant can be formed into sinusoid or other waveform strut members to control and promote elongation, expansion or contraction along single or multiple axes. As such, controlled and designated stress, tension and compression distribution is promoted across specific or localized areas of the construct. Further, portions of the implant can be coated to provide additional control of expansion, and to protect from or promote tissue in-growth.

The implant can be formed such that regions or portions can include anchoring features to facilitate engagement and attachment of the implant to target tissue sites. In addition to anchoring to internal tissue, it is also possible to have one or more portions of the implant extend out of an incision or orifice in a patient.

Various anchors, without or without extending tines, can be defined, formed or otherwise provided with the implant. The anchors can be integrally formed, cut or otherwise defined with the implant. Portions of the implant or anchors can be adapted to collapse, fold or otherwise deform to some extent to facilitate engagement with an introducer or needle device and/or to facilitate tissue penetration or fixation.

The material and cell construct of the sling implant can be configured to promote flexibility while still providing optimal implant strength and tissue support. Further, the stable geometrical and dimensional attributes of the implant provide a flexible device that can be easily positioned and deployed while also avoiding undesirable implant warping or bunching. Such a configuration generally promotes a sling implant adapted to substantially remain in plane during deployment and tissue fixation.

The sling implants, or portions thereof, can be adapted to provide desirable adjustability, stress distribution, anchoring, stabilization, variable elongation, and the like.

DETAILED DESCRIPTION OF PREFERRED EMBODIMENTS

Referring generally to FIGS. 1-50, various embodiments of patterned sling implants 10 and methods are shown. In general, the implant 10 can include a support portion 12, one or more extension portions 14 and one or more anchoring features 16. The extension portions 14 include the material construct extending from the support portion 12 to the respective anchoring features 16. Various portions of the implant 10 can be constructed of polymer materials, e.g., into a molded generally planar structure or cut from a thin generally planar film or sheet material. Examples of acceptable polymer materials available in constructing or forming the implant systems 10 and its components can include polypropylene, polyethylene, fluoropolymers or like biocompatible materials.

The various implants 10, structures, features and methods detailed herein are envisioned for use with many known implant and repair devices (e.g., for male and female), features and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2010/0261955, 2002/151762 and 2002/147382. Accordingly, the above-identified disclosures are fully incorporated herein by reference in their entirety.

Referring generally to FIGS. 1-20, various embodiments of the sling implant 10 are shown. Portions of the implant 10, such as the support portion 12 and the extension portions 14, can be formed or patterned by way of a polymer molding process to create a unitary homogeneous non-woven, or non-knitted, device or construct. Other embodiments can be formed from an already unitary homogeneous sheet or film via laser cutting, die cutting, stamping and like procedures. In certain incontinence sling embodiments of the implant, the support portion 12 can be configured and shaped for positioning under and support of the urethra or bladder (which includes any location of the bladder, urethra, bladder neck, mid-urethra, or proximal end of the urethra), with the extension portions 14 extendable out to proximate muscle, ligament or other tissue for anchoring. The implant also can be used to support pelvic tissue such as the vaginal tissue, tissue of the perineum, coccygeus, levator ani, levator hiatus, and rectum.

The various length, width and other dimensional characteristics of the implant, portions and components can vary greatly. In exemplary embodiments, the implant width, at any portion, can be approximately 5 mm to 15 mm, and the length from end to end can be approximately 6 cm to 15 cm.

Repeated cells or patterns in the implant 10 generally form a lattice structure. Portions of the implant 10 can be cut into sinusoid, or other waveform or undulating struts 15 patterns to control elongation or compression along single or multiple axes, to define a desirable pattern density with overall reduced surface area, and to control the distribution and shaping from applied loads. The ability to mold, form or cut the struts 15 in a nearly endless array of sinusoidal or like configurations provides an implant 10 that can better tailor or mimic the anisotropic behaviors of physiological tissue. Various patterned implant configurations, features and methods disclosed in U.S. patent application Ser. No. 12/953,268, and filed Nov. 23, 2010, can be included, in whole or in part, with the embodiments of the present invention and is, thereby, incorporated herein by reference in its entirety. Controlled and designated stress distribution is promoted across specific or greater areas of the implant 10. In various embodiments, the film or unitary construct of the implant can have a thickness T of approximately 0.005 inches to 0.020 inches, and the struts 15 can have a width W of approximately 0.005 inches to 0.012 inches. Other configurations, shapes and sizes for the various portions of the implant 10 can be employed as well to promote and facilitate the deployment, use and support of the implant 10 disclosed herein.

In certain embodiments, such as those depicted in FIGS. 1-8, the patterned struts 15 define a general pinwheel design including first angular strut lines 20 and second angular strut lines 22 crossing or intersecting at repeating fixed junctions 24 to define cellular voids 26. The thickness, size and separation of the struts 15 can be modified to create an implant 10 with different surface area and cellular density attributes. The struts 15 can have uniform or variable widths or thicknesses, can be tapered, can include apertures, or can include defined shapes and/or patterns, e.g., sinusoids, squares, elliptical, triangular, elbowed, straight, or other simple or complex shapes and patterns. Unique strut 15 designs and cellular patterns can be included within a single implant 10 to provide different zones, having different stress, load distribution or compression characteristics. Other strut 15 designs and patterns can be employed as well to achieve the functionality described and depicted herein.

The dimensional design of the implant struts 15 can be configured to promote targeted strength and flexibility. For instance, the material width at the fixed junctions 24 can be measurably greater than the material width W of the struts 15 intermediate the junctions to allow for increased strength at the junctions. Strengthened and widened junctions 24 can handle and absorb greater stress or torque resulting from implant positioning, twisting and general manipulation. Conversely, thinner strut portions intermediate the junctions 24 promote increased flexibility and controllability of the implant 10 during positioning and device manipulation. This flexibility will also provide an implant 10 adapted to properly conform to unique patient anatomy and lay flat against such anatomy to provide optimal support distribution, tissue in-growth and like characteristics. Other dimensional ranges and proportions are envisioned for embodiments of the struts and strut portions depending on the particular application, strength, flexibility, stress distribution or other performance needs of the implant.

Additional benefits are presented with the homogenous non-woven design and targeted strength regions (e.g., fixed junctions) of the implant 10. Namely, a flexible but strong implant 10 is provided, while still maintaining a low surface area, lower inflammatory response, less scarring and increased density.

The patterned sling implant 10 also provides benefits over traditional knitted or woven mesh in the area of compression and the reaction to longitudinal extension strain. Traditional knitted or woven mesh implants can tend to compress, narrow, bunch or fold during longitudinal stretching, thereby displaying a positive Poisson affect or ratio. Conversely, the sinusoidal pinwheel cell and strut configurations of the patterned implants 10 of embodiments of the present invention can display a Negative Poisson affect or ratio. In particular, as the implant 10 is loaded or stretched (e.g., at ends, anchors, corners or upon the planar surfaces), the strut and cell structures resist compression and can measurably expand to provide a stable and generally planar surface area for tissue or organ support. The combination of the struts and fixed junctions facilitate this Negative Poisson affect.

Figure 1:
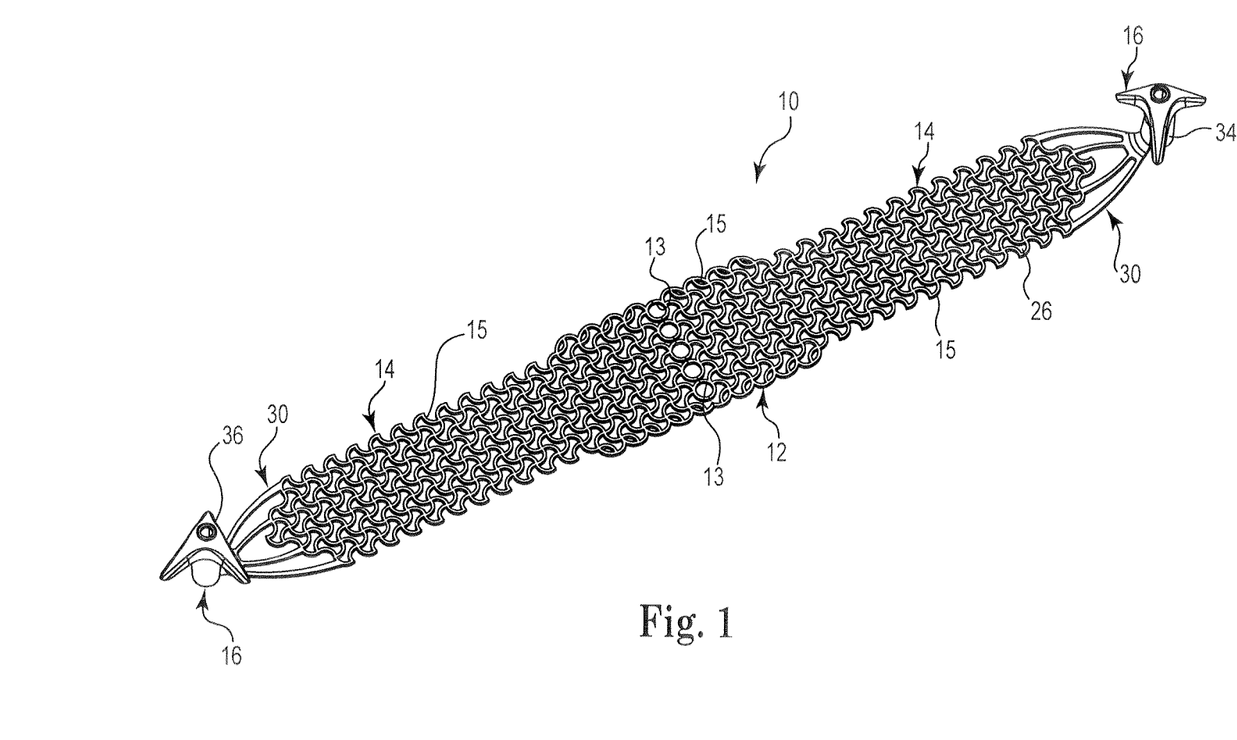
FIG. 1 is a perspective view of a unitary patterned sling implant having generally transverse extending anchoring features in accordance with embodiments of the present invention.
Figures 2, 4:
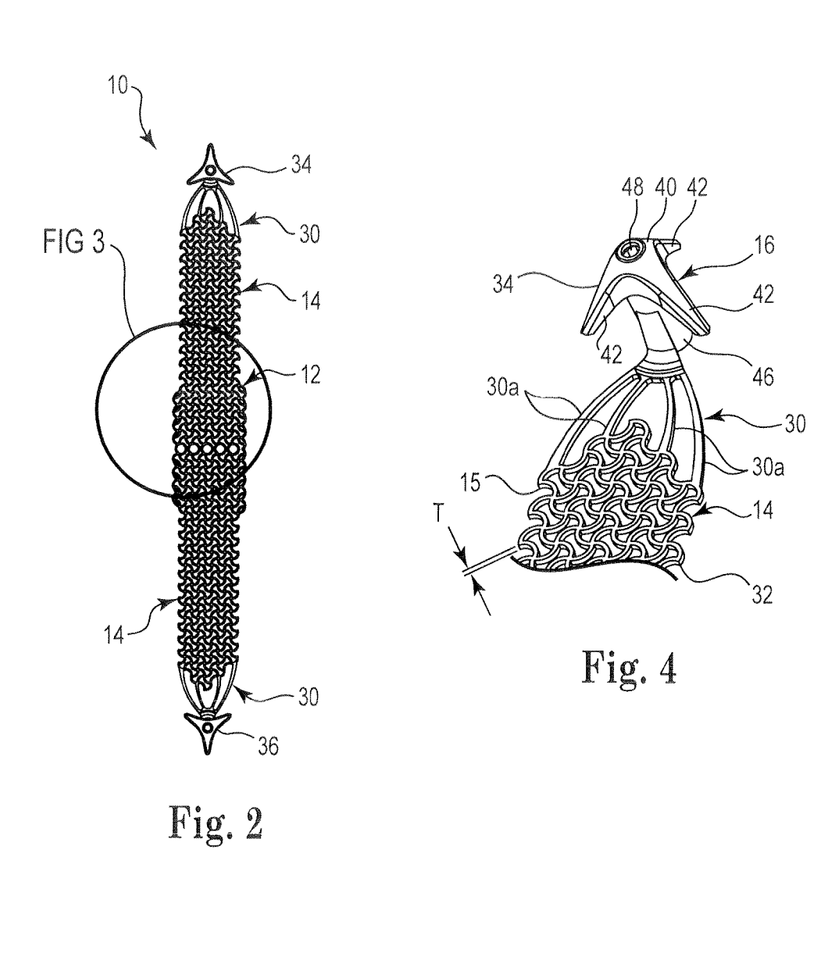
FIG. 2 is a top view of the unitary patterned sling implant of FIG. 1.
FIG. 4 is a close-up partial view of an anchoring feature, transition zone and extension portion of a unitary patterned sling implant in accordance with embodiments of the present invention.
Figure 3:
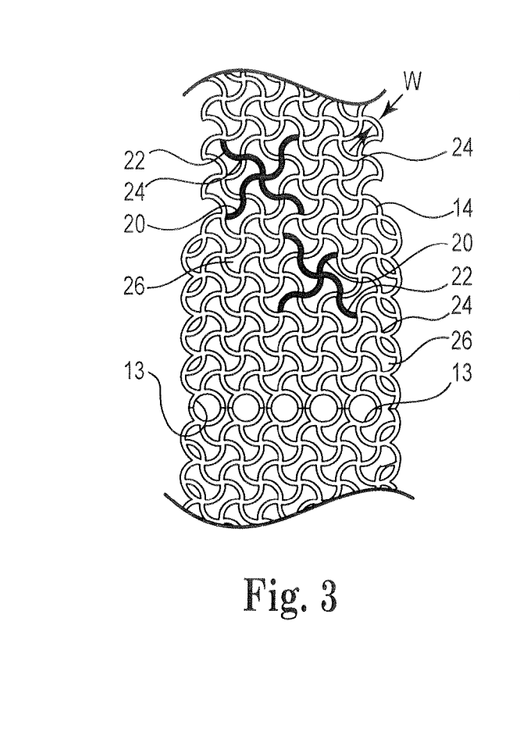
FIG. 3 is a close-up partial view of a portion of the unitary patterned sling implant of FIG. 2.
Figure 5:
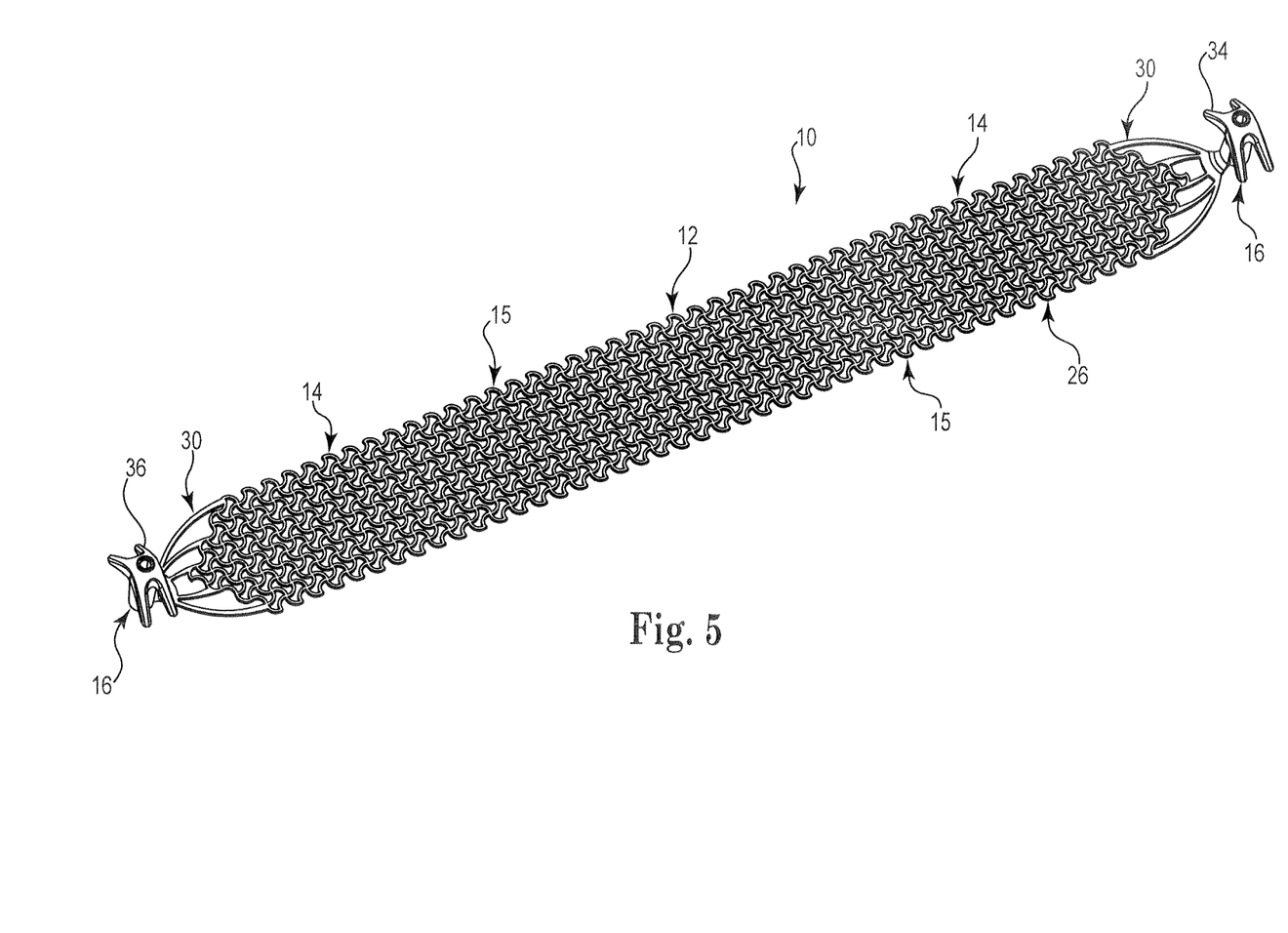
FIG. 5 is a perspective view of a unitary patterned sling implant having generally transverse extending anchoring features in accordance with embodiments of the present invention.
Figure 6:
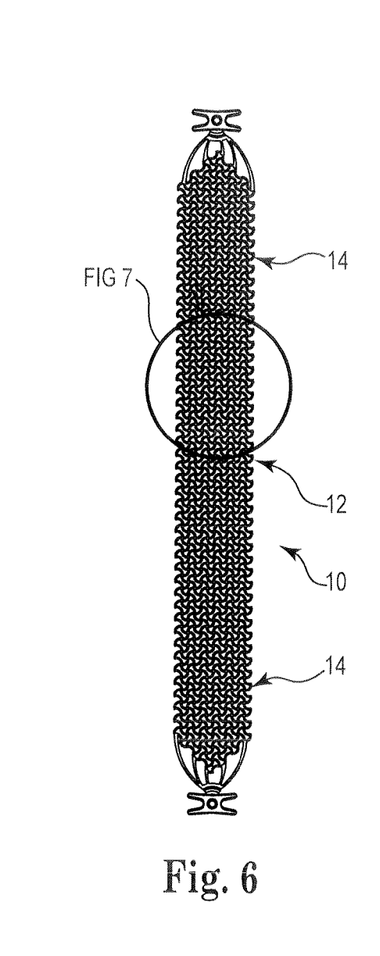
FIG. 6 is a top view of the unitary patterned sling implant of FIG. 5.
Figure 7:
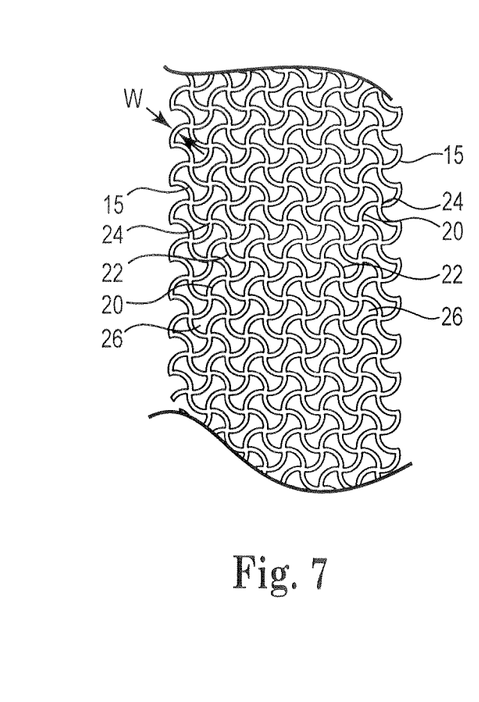
FIG. 7 is a close-up partial view of a portion of the unitary patterned sling implant of FIG. 6.

As shown in FIGS. 1-3, the support portion 12 can take on physical and design characteristics to promote tissue or organ support, and to reduce or eliminate undesirable erosion. The support portion 12 can be measurably wider than the extension portions 14 in certain embodiments. Relatively narrow extension portions 14 can promote flexibility and positioning of the implant 10 within the patient, without jeopardizing the size and effectiveness of the support portion 12. In other embodiments, the support portion 12 can include one or more apertures 13 adapted to reduce tissue erosion, and to promote tissue in-growth, flexibility and tissue support.

Figure 8:
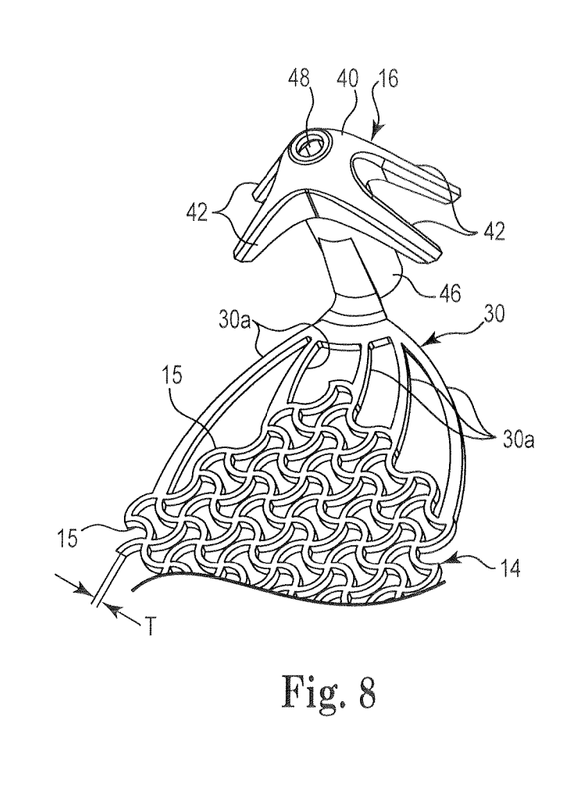
FIG. 8 is a close-up partial view of an anchoring feature, transition zone and extension portion of a unitary patterned sling implant in accordance with embodiments of the present invention.

Embodiments of the implant 10 can include one or more transition portions or zones 30, as shown particularly in FIGS. 4 and 8. In general, the zones 30 provide a material transition between the cellular construct of the extension portions 14 and anchoring or like features of the implant 10, e.g., anchors, eyelets, etc. The transition zones 30 can take on various sizes, shapes and designs to provide increased strength and stress absorption/distribution for portions of the implant 10 being pulled, pushed and twisted during deployment and positioning of the implant 10. Embodiments of the zones 30 can include arcuate or linear members 30a extending out from or into the extension portions 14 and the anchoring portions 16. The members can be tapered into or away from the extension portion 14 or anchoring portion 16 to facilitate stress and tension distribution such that the struts 15 and cell structures of the extension portion 14, or support portion 12, are protected from tearing, ripping or other material breaches. Such a design further provides beneficial flexibility and manipulation characteristics during deployment.

The embodiments of FIGS. 9-20, and 23-34 demonstrate implants 10 and/or implant cell portions having various linear, angled and shaped struts 15 to define unique patterned cell configurations. Again, the thickness, size, shape and separation of the struts 15 can be modified to create an implant 10 with different surface area, void or pore shapes/sizes, and cellular density attributes. As shown in FIGS. 9, 12, 15 and 18, the support portion 12 can take on a different pattern or size configuration than the extension portions 14 to facilitate support, reduce erosion and bunching, or to promote like considerations. As shown in FIGS. 23-34, the strut cell patterns can be separated or symmetrically distributed by way of various spacer elements 15a. The width, length, shape, number and distribution of the spacer elements 15a joining the geometric voids may be varied to achieve desired mechanical characteristics. Using principals of symmetry, implants 10 can be provided in which mechanical characteristics are uniform within the plane of the implant 10 regardless of the direction of an applied stress (e.g., isotropic). Alternatively, the implant 10 (e.g., support portion 12 or extension portions 14) may be configured so that mechanical properties differ substantially along selected axes.

Further, the implant 10 can be formed or cut such that certain edges or other portions can include edge features 32, e.g., teeth, tines, tangs, angled portions, wisps, members, strut portions, stabilizers or other like features to provide capture points for materials or tissue that pass proximate the implant, or to serve as a means of assistive tissue anchoring during or after deployment of the implant 10.

The shaped or cut cells, or patterns, can be configured to optimize or increase tissue in-growth, to promote load bearing along select portions of the implant, and to compensate for stiffness, elongation, tensile strength and warping or bunching resistance. The implant 10 (e.g., portions 12, 14) can include a plurality of protuberances or nubs generally extending and lying within the cell structure or strut 15 construct of the implant 10. One or more of the nubs can be included within any, or all, of the defined cell voids 26. The nubs can extend substantially along the same plane as the implant 10, or generally transverse to that plane. The nubs can provide increased load support and contact points while not substantially increasing the surface area of the implant 10.

The structure and design of the anchoring features 16 of the implant 10 can vary greatly depending on the particular implantation and support needs of the particular sling device (e.g., FIGS. 4, 8 11, 14, 17 and 20). In certain embodiments, the anchor portions 16 can include first and second end anchors 34, 36 extending out from the implant 10.

The anchoring features 16, such as the end anchors 34, 36, can be formed (e.g., molded), cut or otherwise defined integrally with the unitary implant 10. The anchors 16 can include a distal end 40 adapted to penetrate or otherwise engage tissue within the patient, and one or more extending (e.g., angled, straight, curved, etc.) tines or barbs 42 to facilitate tissue fixation. The tines 42 can be generally flexible or deformable to allow for compression or collapsibility when a level of force is applied at the top of the tines 42. Once the tissue catches the tip of the tines 42, or force is applied from the underside of the tines 42, the tines 42 expand to fixate to the tissue. In exemplary embodiments, the anchor width (e.g., tine tip to tip) can be approximately 4 mm to 8 mm, and the anchor length (e.g., tip to tail) can be approximately 5 mm to 10 mm.

Various embodiments of the anchors 16 can further include a barrel or body portion 46, as shown in FIGS. 4 and 8. The body portion 46 can include an interior lumen 48 adapted to selectively engage with an insertion or introduction tool (e.g., insertion needle tip). As shown in FIGS. 1-8, the anchors 16 can extend out generally transverse from the plane of the extension portions 14 of the sling implant 10. Such an anchor design is adapted to decrease insertion force while also increasing desirable holding force within the tissue. As shown in FIGS. 9-20, the anchors 16 can extend out from and generally along the same plane as the extension portions 14 of the sling implant 10.

Figure 9:
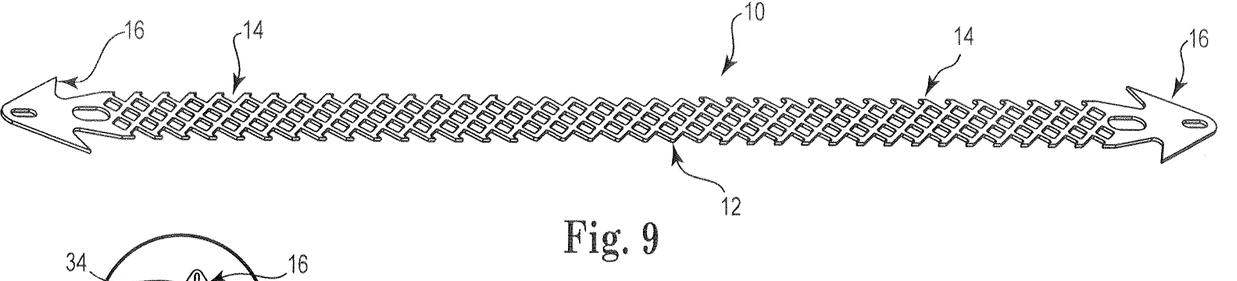
FIG. 9 is a perspective view of a unitary patterned sling implant having planar extending anchoring features in accordance with embodiments of the present invention.
Figure 10:
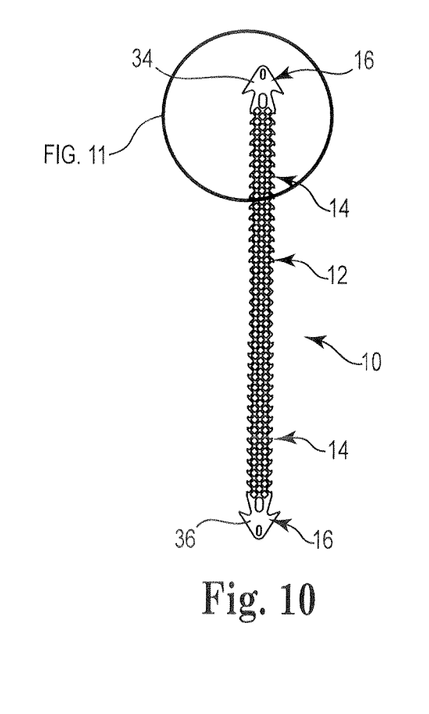
FIG. 10 is a top view of the unitary patterned sling implant of FIG. 9.
Figure 11:
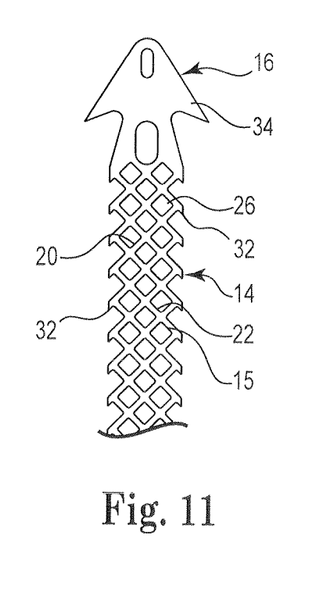
FIG. 11 is a close-up partial view of a portion of the unitary patterned sling implant of FIG. 10.
Figure 12:
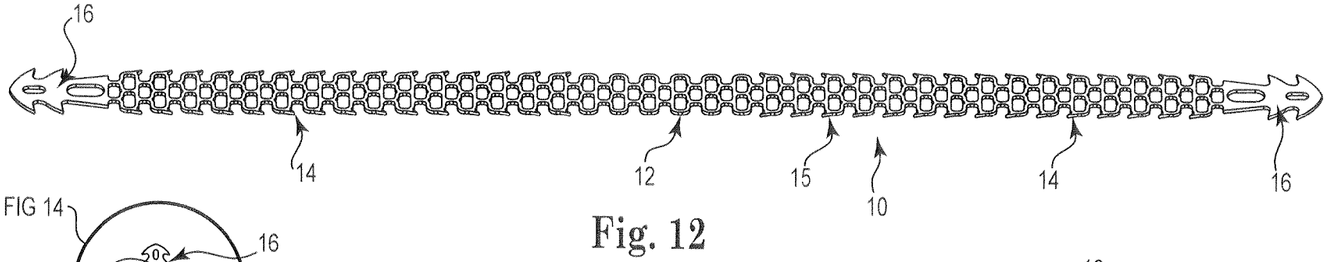
FIG. 12 is a perspective view of a unitary patterned sling implant having planar extending anchoring features in accordance with embodiments of the present invention.
Figure 13:
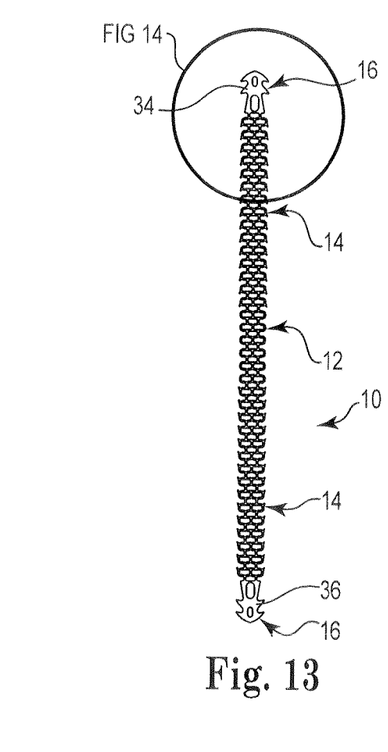
FIG. 13 is a top view of the unitary patterned sling implant of FIG. 12.
Figure 14:
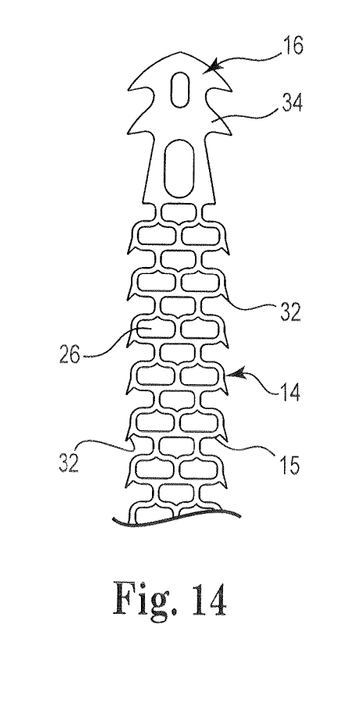
FIG. 14 is a close-up partial view of a portion of the unitary patterned sling implant of FIG. 13.
Figures 15, 16, 17:
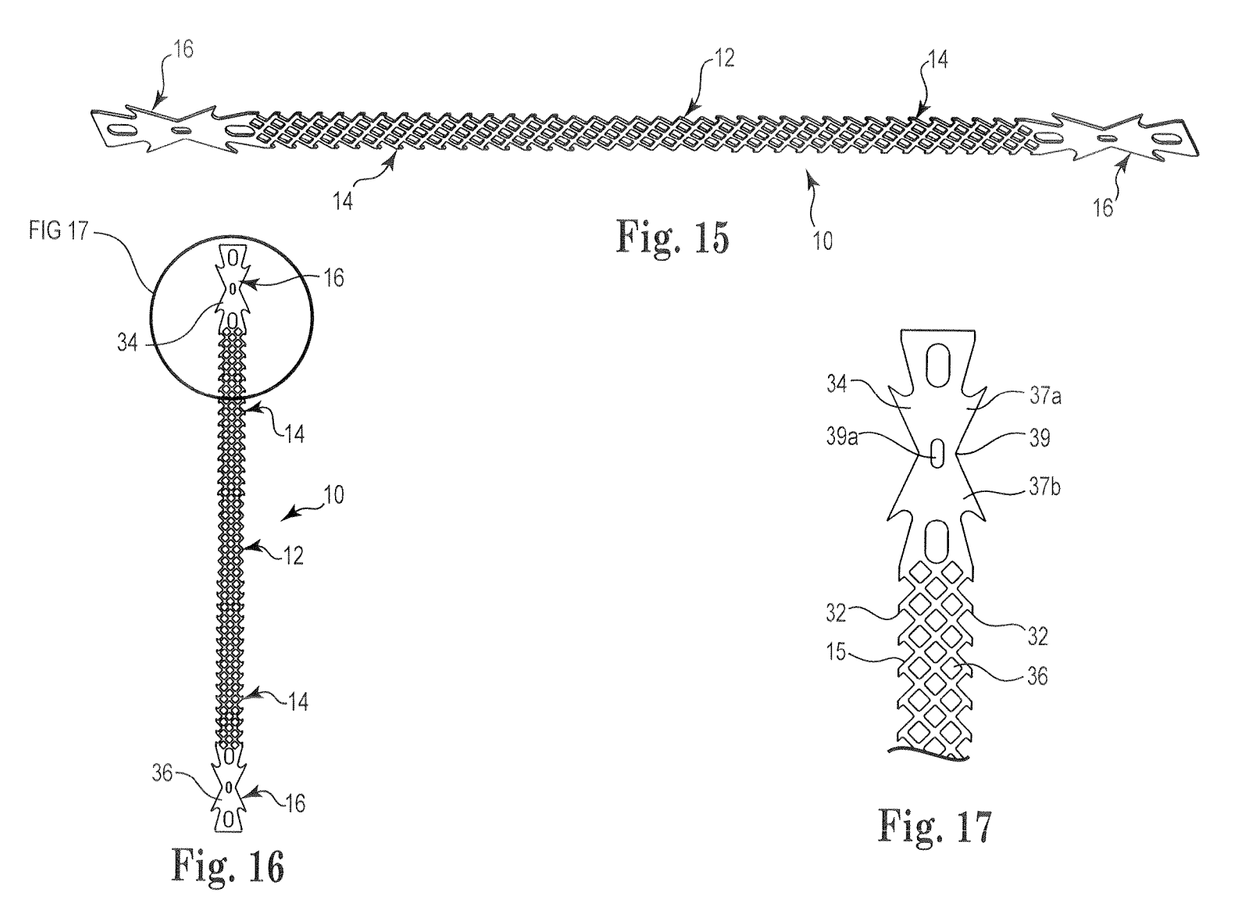
FIG. 15 is a perspective view of a unitary patterned sling implant having planar extending anchoring features in accordance with embodiments of the present invention.
FIG. 16 is a top view of the unitary patterned sling implant of FIG. 15.
FIG. 17 is a close-up partial view of a portion of the unitary patterned sling implant of FIG. 16.
Figures 18, 19, 20:
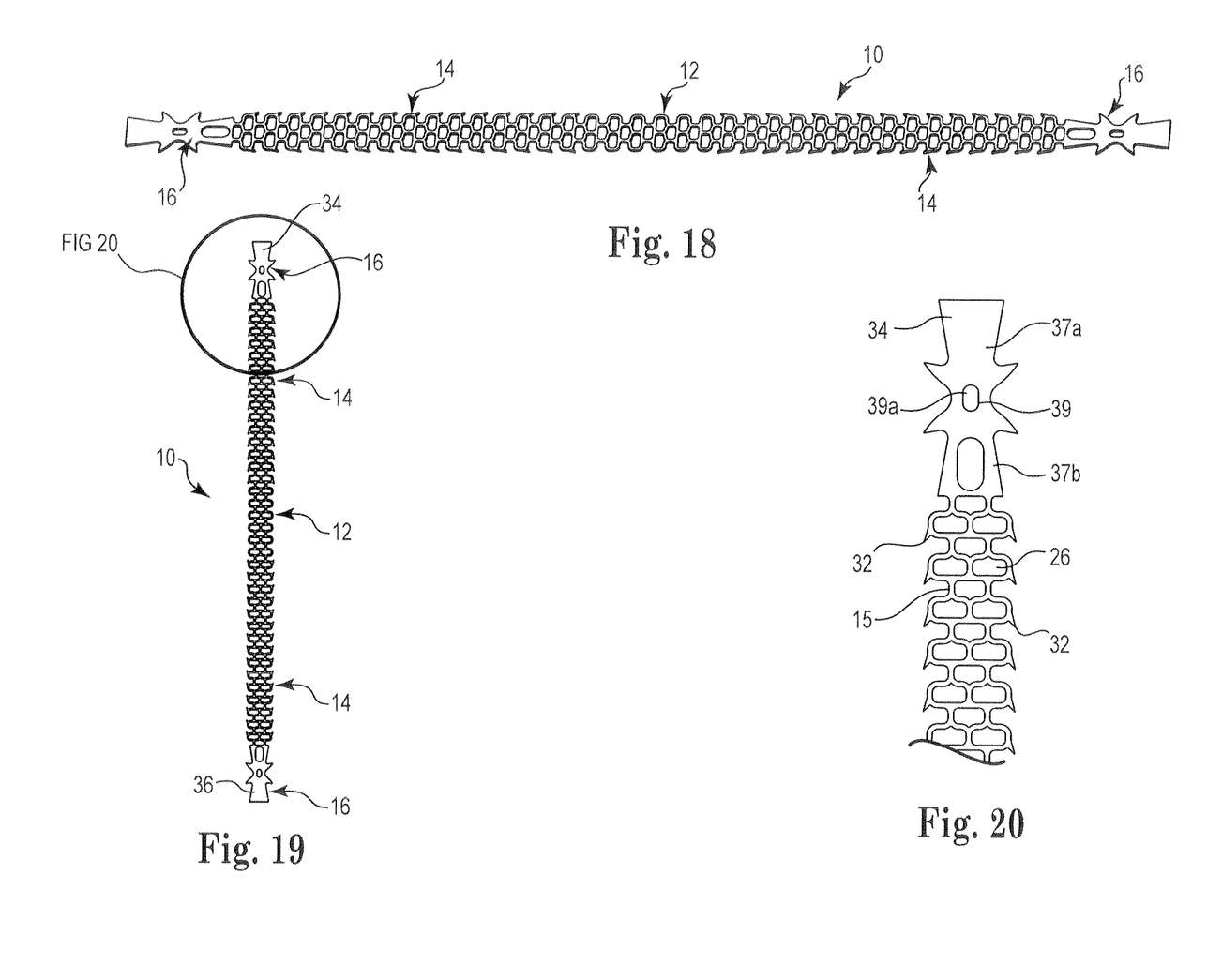
FIG. 18 is a perspective view of a unitary patterned sling implant having planar extending anchoring features in accordance with embodiments of the present invention.
FIG. 19 is a top view of the unitary patterned sling implant of FIG. 18.
FIG. 20 is a close-up partial view of a portion of the unitary patterned sling implant of FIG. 19.

Embodiments of the anchoring features 16, such as those depicted in FIGS. 9-10, can be formed or cut into relatively thin (e.g., relative to the thickness of the support portion 12 or extension portions 14) anchors 34, 36. As shown in FIGS. 15-20, the anchors 34, 36 can define two generally mirroring portions 37a, 37b. The portions 37a, 37b can be adapted to fold on each other about a central portion 39 to create a generally 3-D anchor such that a needle or other introducer device is attachable to the anchoring feature 16 (e.g., at a feature, structure or aperture 39a) at or proximate the central portion 39, or any other portion of the anchoring features 16.

Any of the anchoring features 16 can include various apertures, slits, lumens, barrels, clips, snaps, structures or regions to facilitate or accommodate connection or selective engagement with a needle or other introducer device. In addition, the anchoring features 16 can be formed integral with or separately coupled with the implant 10 or extension portions 14.

In addition to the anchoring portions 16 depicted herein, other configurations are also envisioned. For instance, the anchors 34, 36 can be rotatably or pivotably affixed to the sling implant 10.

Various embodiments of implant 10 can include markings or indicia to indicate lines or sections to assist in deployment, positioning and adjustment. In addition, scoring, indenting, crushing and like procedures or features can be included along one or more portions of the implant 10 to indicate trimming or sizing lines or zones.

In addition to molding or laser cutting portions of the implant 10, punching, die cutting, 3-D printing and other methods and techniques can be used to form or define the implant 10. Portions of the implant 10 can be coated to provide additional control of expansion, and to protect from or promote tissue in-growth. The material surface or surfaces of the implant 10 or cells can be smooth or rough to promote mechanical or tissue in-growth characteristics.

The ability to form or cut the support and extension portions 12, 14, or other portions of the implant 10, in a nearly endless array of configurations provides an implant that can better tailor or mimic the anisotropic behaviors of physiological tissue. This also can provide a sling implant 10 having significantly less surface area than traditional mesh implants.

These configurations for the patterned sling implant 10 can assist in maintaining the implant in a generally flat or pre-defined plane or position during deployment, which will in turn make placement easier for the physician and reduce incidence of pain syndromes, erosion, etc.

By arranging the density of the cell patterns with the embodiments of the implants 10 of the present invention, it is possible to tailor the elongation, load or strength properties of the implant 10 according to specific needs and support requirements. Moreover, more than one material can be used to construct the implant 10 to further control desired load and stress properties, e.g., combining different polymers such as polypropylene, PEEK, PET, PTFE, PGA, PLA, etc. Polymers could also be combined with metallic elements to alter strength and elongation profiles of the implant 10. The stronger materials would take up stresses from higher load regions faster, thereby allowing for a method to selectively control performance characteristics of the implant 10. Moreover, a polymer or metal frame or feature could be provided along the periphery or other select areas of the implant 10 to provide additional strength or rigidity properties.

As detailed herein, various structures and components of the present invention can be integrally formed into a unitary body via a molding process. For instance, an injection molding machine (e.g., Milacron Roboshot S2000i 33B machine) having internal vacuum and cooling lines can be employed. In general, a dry resin, such as a polypropylene resin, is maintained at high temperatures for several hours. In addition, the mold device can be heated. Then, the mold vacuum lines can be started and the injection molding cycle initiated. The mold cavities will be filled and the device will be cooled for a period of time. Upon completion, the mold is opened and part ejection will activate with evacuation. The mold can then be closed and the cycle repeated for additional injection molded implants. Other known molding processes and systems can be employed with the present invention as well.

Other embodiments of the implant 10 can be formed or cut along a precise cutting tool path (e.g., using the DPSS 266 laser system), to cut the implant 10 and strut 15 features and designs in an already unitary film or sheet of polymer material. Alternatively, the implant features and portions can be stamped into such a unitary film or sheet material.

Referring generally to FIGS. 35-50, various implant 10 portions and methods of forming such portions are disclosed to facilitate preferential or targeted tear zones 50. The implant 10 can, therefore, include portions that can be removed by the physician or other users according to the patient's unique anatomical makeup, surgical requirements, and the like. In general, a direct extrusion or 3-D printing method is employed such that a polymer is extruded or printed onto a surface to create a structure or construct of the implant 10 to form the tear zones 50. These tear zones 50 allow for a structure that can be pulled apart in a controlled manner. This is useful in applications where a portion of the structure or implant 10 is not needed and can be removed with or without the need for a cutting instrument. As such, damage that might occur to the structure or portion of the implant 10 by using a cutting instrument can be avoided if so desired.

Figure 46:
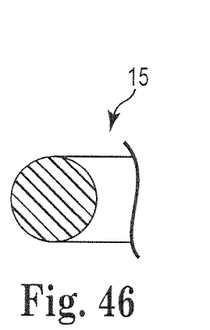
Figure 47:
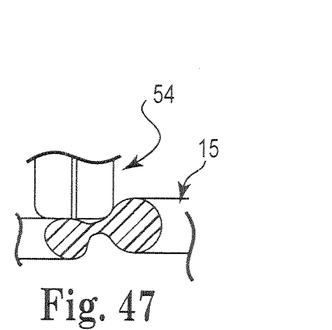
Figure 48:
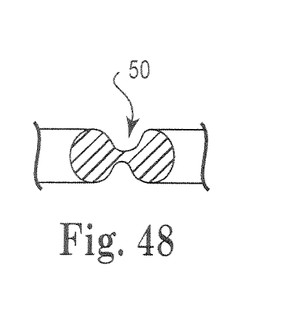
Figure 49:
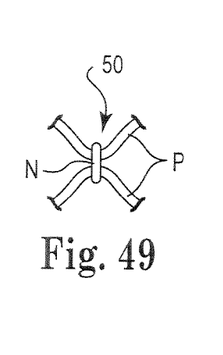
Figure 50:
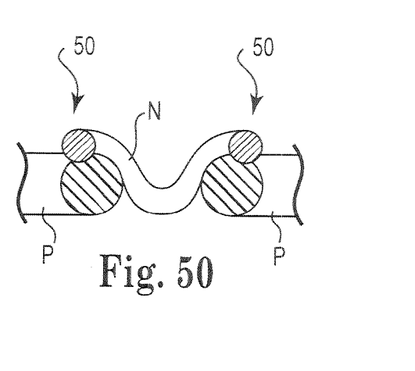

The direct extrusion or 3D printing method creates the structure by pushing a thermoplastic above the melting point and out of a small orifice or nozzle device 54, as shown in FIGS. 46-48. The extruded hot plastic is then "drawn" or otherwise provided on a surface of the implant (e.g., strut, film, etc.) to create a tear structure, where the extrudant forms a thin single tear strut, structure or feature 52 in the design or at a portion of the implant 10. By controlling how the extrudant bonds to previously extruded or formed materials, the bond strength can be controlled to create zones for pre-defined tearing. These zones 50 or tear structures/struts 52 can be increased in size or thickness when more force is required to facilitate tearing or separation, or can be formed relatively thin when less separation or tearing force is desired.

As shown in FIGS. 38-50, certain methods for controlling bond strength of the zones 50 can include controlling the amount of physical overlap PO between the new extrudant N and the previously laid down material P, and controlling the time the heated extruder nozzle dwells on the previously laid down material P to cause significant re-melting and joining flow of the material P with the new extrudent N. Further, bond strength can be controlled by varying the number of individual extrudant strands or bonds that make up a strut (e.g., FIGS. 41-45, 49-50), and by bridging the new extrudant N to the previously laid down material P. Bridging can occur when the nozzle device 54 presses into the previously laid down material P to re-melt and flow a small portion of it into a thin bridge of material that bonds to the new extrudant N, as shown in FIGS. 47-50. Other known extrusion, molding, printing or like formation methods and techniques are also envisioned for use in defining predefined tear zones 50 in portions of the implant 10.

The implants 10 described herein can be implanted into a patient by use of various different types of surgical tools, including insertion tools, which generally are tools useful to engage and place a tissue anchor and elongate incontinence sling. Various types of insertion tools are known, including those in the previously-incorporated references, and these types of tools and modifications thereof can be used according to the present description to install the sling implant 10.

Figure 21:
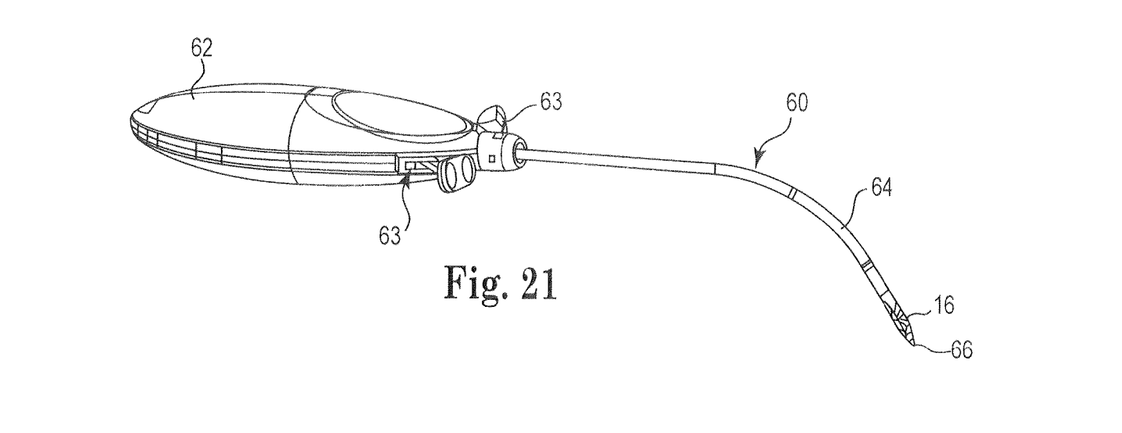
FIGS. 21-22 show exemplary sling introduction tools in accordance with embodiments of the present invention.
Figure 22:
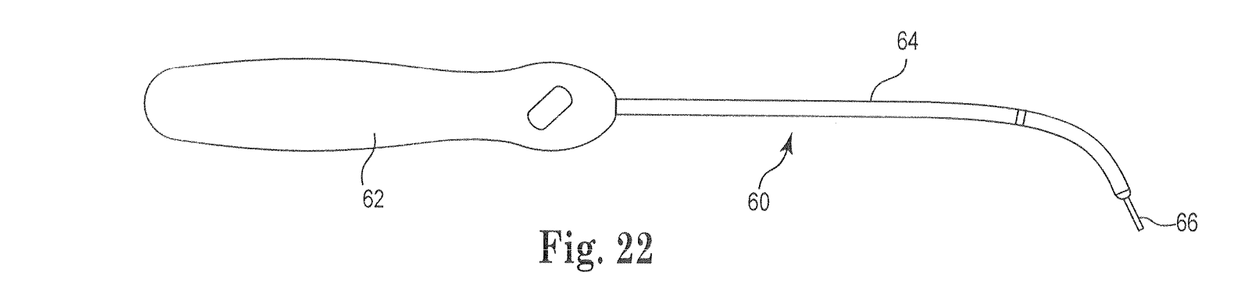
Figure 23:
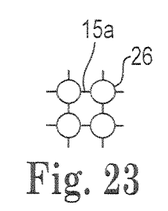
FIGS. 23-34 show various patterned cell configurations and spacer elements for sling implants in accordance with embodiments of the present invention.
Figure 24:
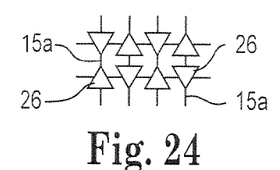
Figure 25:
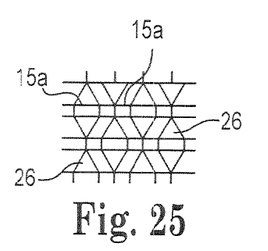
Figure 26:
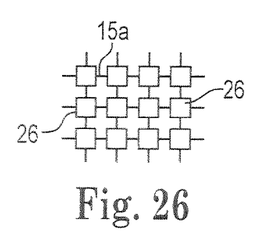
Figure 27:
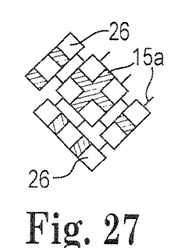
Figure 28:
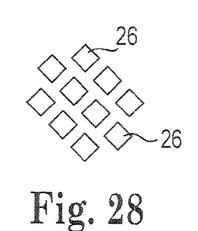
Figure 29:
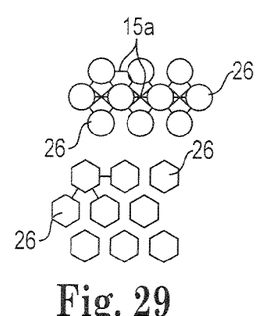
Figure 30:
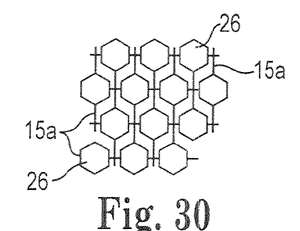
Figure 31:
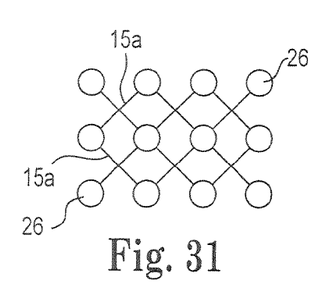
Figure 32:
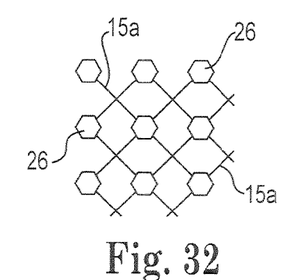
Figure 33:
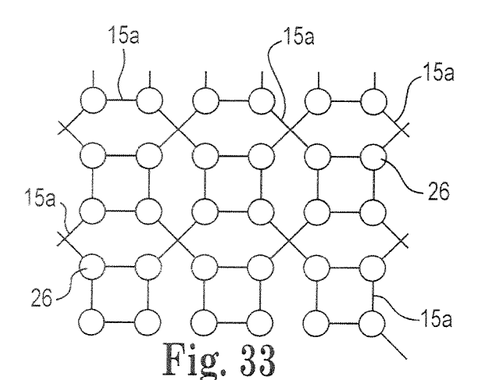
Figure 34:
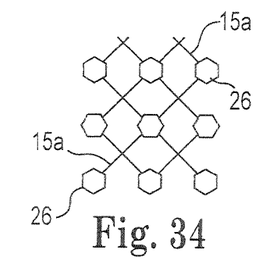
Figure 35:
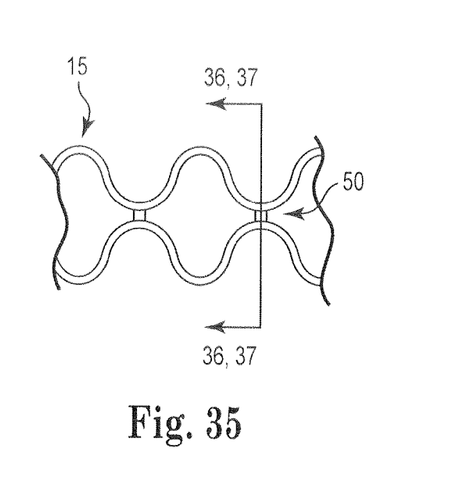
FIGS. 35-50 show various tear zones, structures and methods for sling implants in accordance with embodiments of the present invention.
Figures 36, 37:
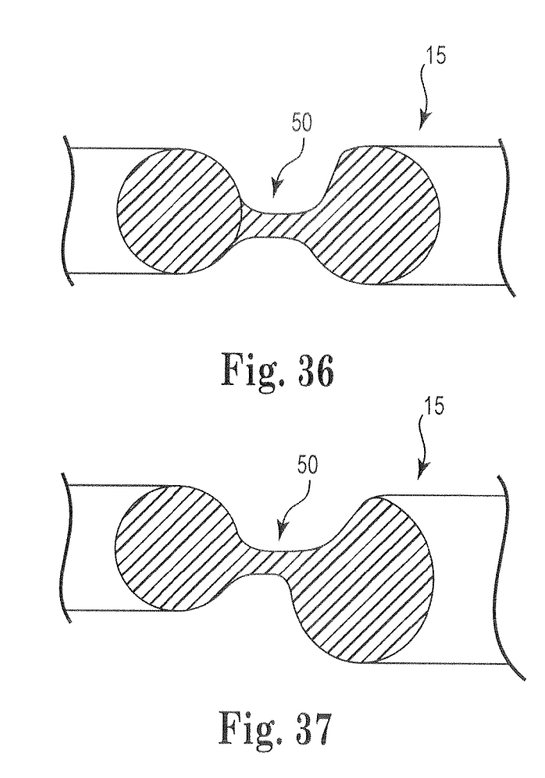
Figure 38:
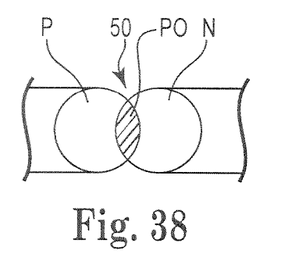
Figure 39:
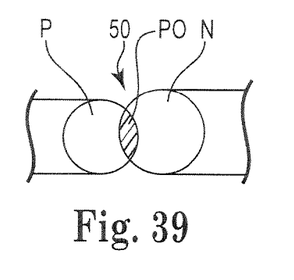
Figure 40:
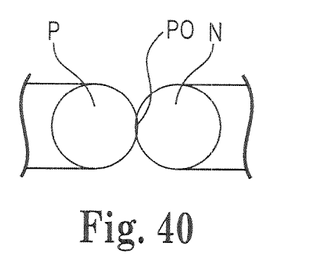
Figure 41:
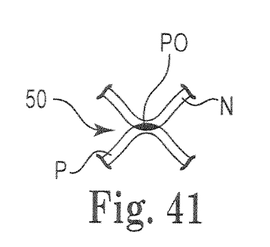
Figure 42:
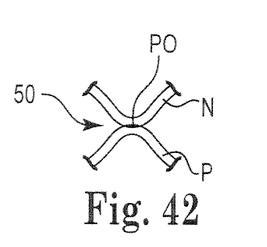
Figures 43, 44:
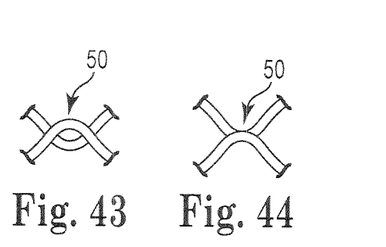
Figure 45:
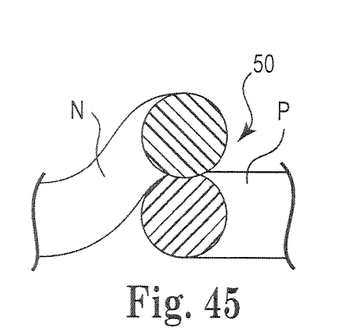

Exemplary insertion tools are shown in FIGS. 21-22. Each tool 60 can include a handle 62, needle 64 and engaging distal tip 66. The handle 62 can include an actuation mechanism 63 in operative communication with the distal tip 66 and adapted to selectively control engagement and/or disengagement of the distal tip 66 with portions of the implant 10 (e.g., anchors 16). The needle 64 can be helical, straight, or curved, to name a few options. A portion of the needle 64, such as the needle tip 66, can include one or more barb guards adapted to receive or abut against the one or more tines 42 of the anchors 16 to protect from undesirable tissue contact or penetration during initial deployment and positioning of the implant 10 (e.g., prior to target tissue fixation).

Embodiments of the present invention can be implanted in a patient to treat incontinence, such as urinary incontinence. The tool 60 (e.g., needle 64) can be inserted through an incision that provides access to the pelvic region. The incision may be, for example, a vaginal incision (for female anatomy), a perineal incision (for male anatomy), or an incision in the rectal or buttock region, inner thigh or groin, pubic region, etc. The needle tip 66 can be connected to a first of the anchor features 16 (e.g., anchor 34) and placed at a desired location for fixation of the anchoring feature 16 to target tissue, such as at an obturator foramen. The other of the anchor features 16 (e.g., anchor 36) can be bilaterally deployed and fixated (e.g., to the obturator foramen) on the other side of the supported organ. The support portion 12 can then be adjusted and tensioned relative to the supported organ/tissue (e.g., urethra or bladder) as needed.

The implants 10, their various components, structures, features, materials and methods may have a number of suitable configurations as shown and described in the previously-incorporated references. Various methods and tools for introducing, deploying, anchoring and manipulating implants to treat incontinence (e.g., male and female) as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. A unitary patterned implant for treating incontinence in a patient, comprising:
   a non-woven unitary elongate sling having:
      a support portion including a plurality of strut members joined at and spanning out from a plurality of fixed junctions, the support portion defined along a first plane;
      first and second extension portions;
      at least one tissue anchor having one or more deformable tines adapted for fixation to soft tissue of the patient; and
      a transition strength zone including a plurality of elongate arcuate members, an end of each arcuate member integrally formed with the at least one tissue anchor, the transition strength zone extending from and generally along the same plane as one of the first and second extension portions, and between the at least one tissue anchor and one of the first and second extension portions, to facilitate stress or tension distribution between the at least one tissue anchor and one of the first and second extension portions, wherein the at least one tissue anchor is integrally formed with the transition strength zone and one of the first and second extension portions.

2. The implant of claim 1, wherein the at least one tissue anchor extends out generally transverse from the first plane of the support portion and the one or more deformable tines extend out generally transverse from the at least one tissue anchor along a second plane generally parallel with the first plane of the support portion.

3. The implant of claim 1, wherein the at least one anchor extends out generally in plane with the first plane of the support portion.

4. The implant of claim 3, wherein the at least one anchor is substantially equal in thickness to at least one of the first and second extension portions.

5. The implant of claim 1, wherein the at least one anchor includes two opposing end anchors.

6. The implant of claim 1, wherein the plurality of strut members are sinusoidal shaped to define a plurality of pinwheel cell configurations.

7. The implant of claim 1, wherein the at least one anchor includes a body lumen adapted to receive the distal end of a needle tool.

8. The implant of claim 1, wherein the plurality of strut members includes one or more edge retention features extending to provide tissue engagement.

9. The implant of claim 1, wherein the support portion is generally wider than the first and second extension portions.

10. A unitary patterned implant system for treating incontinence in a patient, comprising:
   a non-woven unitary elongate sling including:
      a support portion having a plurality of undulating strut members joined at and spanning out from a plurality of fixed junctions;
      first and second extension portions;
      first and second end anchors extending from respective of the first and second extension portions, the first and second anchors having extending flexible tines adapted for fixation to soft tissue of the patient;
      a transition strength zone including a plurality of elongate arcuate members, an end of each arcuate member integrally formed with the at least one tissue anchor, the transition strength zone extending from and generally along the same plane as the first extension portion, and between the first end anchor and the first extension portion, to facilitate stress or tension distribution, wherein at least the first end anchor is integrally formed with the transition strength zone and the first extension portion; and an introducer needle tool having a handle portion and a needle, wherein the needle includes a distal tip adapted to selectively engage with the first or second end anchors to facilitate deployment and tissue fixation.

11. The system of claim 10, wherein the first and second end anchors are substantially equal in thickness to the first and second extension portions.

12. The system of claim 10, wherein the plurality of undulating strut members are sinusoidal shaped to define a plurality of pinwheel cell configurations.

13. The system of claim 10, wherein at least one of the first and second end anchors includes a body lumen adapted to receive the distal tip of the introducer needle tool.

14. The system of claim 10, wherein the plurality of undulating strut members include one or more edge retention features extending to provide tissue engagement.

15. The system of claim 10, wherein the support portion is generally wider than the first and second extension portions.

16. The system of claim 10, wherein the support portion is generally narrower than the first and second extension portions.

17. The system of claim 10, wherein the introducer needle tool includes an actuation mechanism in operable communication with the distal tip to facilitate selective disengagement of the first or second end anchors.

18. The system of claim 10, wherein the needle of the introducer needle tool is generally curved.

* * * * *